July 11, 1961 D. H. MOREY, JR Plant Pat. 2,072
ROSE PLANT
Filed Oct. 3, 1960
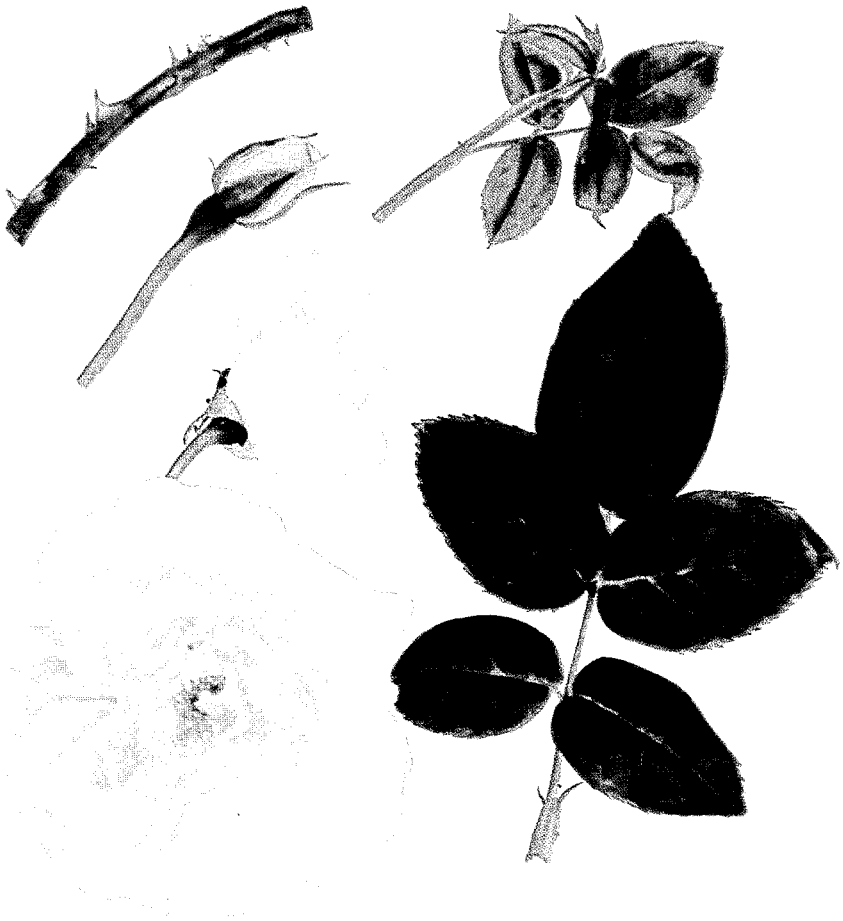
Inventor.
Dennison H. Morey, Jr.
By: Robb & Robb
Attorneys United States Patent Office Plant Pat. 2,072
Patented July 11, 1961

2,072
ROSE PLANT

Dennison H. Morey, Jr., Pleasanton, Calif., assignor to Jackson & Perkins Company, Newark, N.Y., a corporation of New York Filed Oct. 3, 1960, Ser. No. 60,234
1 Claim. (Cl. 47—61)

The present invention relates to a new and distinct variety of rose plant of the climber class, which was originated by me by crossing the variety "Sungold" (unpatentend) with the variety "Sutter's Gold" (Plant Patent No. 885).

The primary objective of this breeding was to produce a new rose variety of the large-flowered climbing hybrid tea type which bears flowers of a color different from that of any other rose of this type. This objective was fully achieved, along with other desirable improvements, as evidenced by the following unique combination of characteristics which are outstanding in the new variety and which distinguish it from its parents, as well as from all other varieties of which I am aware:

(1) Leathery foliage which stands up very well under all weather conditions;

(2) Large flower size, which is unusual in blooms of any comparable color; and (3) A distinctive and attractive general color tonality of the flowers corresponding to Bittersweet Orange, lightly overcast with Capucine Orange.

Asexual reproduction of the new variety by budding, as performed at Pleasanton, California, and also at Newark, New York, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Sungold."
*Pollen parent.*—"Sutter's Gold."
Classification:
*Botanic.*—Climber.
*Commercial.*—Climber.

*Flower*

(Observations made from specimens grown outdoors at Newark, New York, near mid-afternoon in the early part of the month of July.)

Blooming habit: Recurrent—continuous.
Bud:
*Size.*—Large.
*Form.*—Ovoid; is not affected by wet or hot weather.
*Color.*—When sepals first divide—Scarlet, Plate 1. When petals begin to unfurl—Bittersweet Orange, Plate 2. When half-blown: inside of petals—Bittersweet Orange, Plate 2, lightly overcast with Light Salmon-Orange, Plate 2; reverse of petals—Salmon-Orange, Plate 2, lightly overcast with Light Salmon-Orange, Plate 2.
*Sepals.*—Slight branched; curl back when petals begin to unfurl. Color: inside—Light Fluorite Green, Plate 32; outside—Bice Green, Plate 17.
*Calyx.*—Color—Bice Green, Plate 17. Shape—pear. Size—small. Aspect—smooth. Odor when rubbed—none.
*Peduncle.*—Length—short. Aspect—rough. Strength—erect; heavy. Color—Chromium Green, Plate 32.
*Opening.*—Opens up well; is not affected by adverse weather conditions.

Bloom:
*Size.*—Large. Average size when fully expanded—from 4½ to 5 inches.
*Borne.*—Both singly and several together.
*Stems.*—Medium length; strong.
*Form (when first open).*—Cupped. Permanence—retains its form to the end.
*Petalage.*—Double (full but open center). Number of petals under normal conditions—20.
*Color.*—Center of flower—Bittersweet Orange, Plate 2. Outer petals—Orange-Buff, Plate 3, lightly overcast with Capucine Buff, Plate 3. Base of petals (aiglet)—Empire Yellow, Plate 4. Inside of petals—Bittersweet Orange, Plate 2, lightly overcast with Capucine Orange, Plate 3. Reverse of petals—Capucine Buff, Plate 3. General tonality from a distance—Bittersweet Orange, Plate 2, lightly overcast with Capucine Orange, Plate 3.
*Discoloration.*—General tonality at end of first day—Bittersweet Orange, Plate 2, lightly overcast with Capucine Orange, Plate 3. Second day—Bittersweet Orange, Plate 2, lightly overcast with Orange-Buff, Plate 3. Third day—Bittersweet Orange, Plate 2, lightly overcast with Capucine Buff, Plate 3.
Petals:
*Texture.*—Leathery; is not affected by wet or hot weather.
*Appearance.*—Inside—satiny. Outside—shiny.
*Form.*—Oval; slightly notched.
*Arrangement.* — Imbricated (regularly arranged shingle-like).
*Petaloids in center.*—Few; small.
*Persistence.*—Drop off cleanly.
*Fragrance.*—Moderate. Nature—fruity (russet apple).
*Lasting quality.*—On the plant—long. As cut flower—long.

*Genital organs*

Stamens, anthers: Large; many; regularly arranged around styles. Color—Mikado Orange, Plate 3, edged with Walnut Brown, Plate 28.
Stamens, filaments (threads): Long. Color—Pale Yellow-Orange, Plate 3, with lower half of filament Grenadine, Plate 2.
Pollen: Color—Capucine Buff, Plate 3.
Styles: Bunched; uneven length; short; thin.
Stigmas: Color—Pale Yellow-Orange, Plate 3.
Ovaries: All enclosed in calyx.
Hips: None.
Seeds: None.

*Plant*

Form: Climber.
Growth: Vigorous; upright; attains height of 6 feet.
Foliage: Compound of 3–5 leaflets.
*Size.*—Large.
*Quantity.*—Normal.
*Color.*—New foliage: upper side—Lettuce Green, Plate 5, with edges of petals lightly overcast with Oxblood Red, Plate 1; under side—Oxblood Red, Plate 1, with center of leaf Yellowish Oil Green, Plate 5. Old foliage: upper side—Varley's Green, Plate 18; under side—Light Bice Green, Plate 17.
*Shape.*—Oval pointed.
*Texture.*—Upper side—leathery. Under side—smooth.
*Ribs and veins.*—Ordinary.

*Edge.*—Serrated (saw-toothed).

*Serration.*—Single; small.

*Leaf stem.*—Color—Courge Green, Plate 17. Under side—prickly.

*Stipules.*—Long; bearded.

Wood:

*New wood.*—Color—Lettuce Green, Plate 5. Bark—smooth.

*Old wood.*—Color—Forest Green, Plate 17. Bark—smooth.

Thorns:

*Thorns.*—Quantity: on main stalks from base—many; on laterals from stalk—ordinary. Form—narrow base; medium length; straight. Color (when young)—Carmine, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the climber class, substantially as herein shown and described, characterized particularly as to novelty by the unique combination of leathery foliage which stands up very well under all weather conditions, large flower size, and a distinctive and attractive general color tonality of the flowers corresponding to Bittersweet Orange, lightly overcast with Capucine Orange.

No references cited.